(12) United States Patent
Davis et al.

(10) Patent No.: US 11,497,418 B2
(45) Date of Patent: Nov. 15, 2022

(54) SYSTEM AND METHOD FOR NEUROACTIVITY DETECTION IN INFANTS

(71) Applicant: General Electric Company, Schenectady, NY (US)

(72) Inventors: Cynthia Elizabeth Landberg Davis, Niskayuna, NY (US); Guangliang Zhao, Latham, NY (US); Tzu-Jen Kao, Watervliet, NY (US); Aghogho Obi, Troy, NY (US); Nancy Cecelia Stoffel, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 471 days.

(21) Appl. No.: 16/782,960

(22) Filed: Feb. 5, 2020

(65) Prior Publication Data

US 2021/0236026 A1 Aug. 5, 2021

(51) Int. Cl.
*A61B 6/00* (2006.01)
*G06K 9/00* (2022.01)
*A61B 5/11* (2006.01)
*G06T 7/246* (2017.01)
*A61B 5/00* (2006.01)
*G06T 7/00* (2017.01)
(Continued)

(52) U.S. Cl.
CPC .......... *A61B 5/1128* (2013.01); *A61B 5/0035* (2013.01); *A61B 5/0075* (2013.01); *A61B 5/0077* (2013.01); *A61B 5/4094* (2013.01); *G06T 7/0012* (2013.01); *G06T 7/246* (2017.01); *G06V 40/10* (2022.01); *G06V 40/171* (2022.01); *G06V 40/20* (2022.01); *H04N 5/247* (2013.01); *A61B 2503/04* (2013.01); *A61B 2503/045* (2013.01); *G06T 2207/10016* (2013.01); *G06T 2207/10048* (2013.01); *G06T 2207/30201* (2013.01)

(58) Field of Classification Search
CPC .................................... G06K 9/00; A61B 6/00
USPC ........ 382/100, 103, 106–107, 128–134, 162, 382/168, 173, 181, 199, 219, 224, 254, 382/274, 276, 285–291, 305, 312; 600/558, 473, 301; 348/46
See application file for complete search history.

(56) References Cited

U.S. PATENT DOCUMENTS 6,679,830 B2   1/2004   Kolarovic et al.
7,407,485 B2   8/2008   Huiku
(Continued)

FOREIGN PATENT DOCUMENTS

WO   2018172352 A1   9/2018
WO   2019013456 W    1/2019

OTHER PUBLICATIONS

PCT application PCT/US2021/015380 filed Jan. 28, 2021—International Search Report/Written Opinion dated Mar. 25, 2021, 36 pages.

(Continued)

*Primary Examiner* — Seyed H Azarian
(74) *Attorney, Agent, or Firm* — Fletcher Yoder P.C.

(57) ABSTRACT

A neuroactivity monitoring system includes a camera configured to acquire image data of a patient positioned on the patient support and a monitoring device in communication with the camera. The monitoring device uses the acquired image data of the camera to identify and track patient landmarks, such as facial and/or posture landmarks, and, based on the tracked movement, characterize patient neuroactivity.

9 Claims, 6 Drawing Sheets

(51) Int. Cl.
*H04N 5/247* (2006.01)
*G06V 40/10* (2022.01)
*G06V 40/20* (2022.01)
*G06V 40/16* (2022.01)

(56) References Cited

U.S. PATENT DOCUMENTS

| | | | |
|---|---|---|---|
| 8,708,883 | B2 | 4/2014 | Ten et al. |
| 8,764,650 | B2 | 7/2014 | Schiavenato et al. |
| 9,530,080 | B2 | 12/2016 | Glazer |
| 9,572,740 | B2 | 2/2017 | Bodlaender et al. |
| 9,626,581 | B2 | 4/2017 | Gao et al. |
| 9,980,868 | B2 | 5/2018 | Sabota et al. |
| 10,271,017 | B2 | 4/2019 | Tu et al. |
| 2011/0077548 | A1* | 3/2011 | Torch ............ A61B 5/165 600/558 |
| 2012/0212582 | A1* | 8/2012 | Deutsch ............ G16H 40/20 348/46 |
| 2016/0140386 | A1 | 5/2016 | Yu et al. |
| 2016/0174841 | A1 | 6/2016 | Proud |
| 2016/0210747 | A1 | 7/2016 | Hay |
| 2016/0287098 | A1 | 10/2016 | Pradeep et al. |
| 2017/0173262 | A1* | 6/2017 | Veltz ............ G16H 20/17 |
| 2018/0000407 | A1 | 1/2018 | Johnson et al. |
| 2018/0157902 | A1 | 6/2018 | Tu et al. |
| 2018/0189946 | A1 | 7/2018 | Kusens |
| 2019/0320974 | A1* | 10/2019 | Alzamzmi ............ G16H 50/20 |
| 2019/0341147 | A1* | 11/2019 | Lord ............ A61B 5/4848 |
| 2020/0281480 | A1* | 9/2020 | Tran ............ A61B 5/6813 |
| 2021/0000341 | A1* | 1/2021 | Kuperman ............ A61B 5/1122 |

OTHER PUBLICATIONS

WO2019013456 English Translation of Abstract; Espacenet.com search results Apr. 23, 2021.

Karayiannis et al., "Automated Detection of Videotaped Neonatal Seizures of Epileptic Origin", Journal of the International League against Epilepsy, vol. 47, Issue: 06, pp. 966-980, Jun. 7, 2006.

Lago et al., "Guidelines for Procedural Pain in the Newborn", Acta Paediatrica, vol. 98, Issue: 06, pp. 932-939, Jun. 2009.

Lende et al., "Value of Video Monitoring for Nocturnal Seizure Detection in a Residential Setting", Journal of the International League against Epilepsy, vol. 57, Issue: 11, pp. 1748-1753, Sep. 30, 2016.

Bruns et al., "Application of an Amplitude-Integrated EEG Monitor (Cerebral Function Monitor) to Neonates", Journal of Visualized Experiments, vol. 127, pp. 01-09, Sep. 6, 2017.

Radhika et al., "Incubator Baby Parameter Sensing and Monitoring", International Journal of Innovative Technology and Exploring Engineering (IJITEE), vol. 08, Issue: 07, pp. 2945-2947, May 2019.

* cited by examiner

SYSTEM AND METHOD FOR NEUROACTIVITY DETECTION IN INFANTS

BACKGROUND

The subject matter disclosed herein relates to neonatal monitoring techniques. More specifically, the subject matter relates to neonatal monitoring techniques that assess infants neuroactivity based on image analysis.

Infants, particularly neonates (i.e., newborns) may require specialized treatment and care due to their small size and still-developing organs and physiological systems. In a hospital setting, such patients may be cared for in a patient incubator that provides a controlled microenvironment to promote infant development. In addition, the infant patient may be assessed using one or more monitoring devices. However, certain physiological events, such as neuroactivity events, are difficult to identify and may involve labor-intensive manual observation of the patient.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a neuroactivity monitoring system is provided that includes a patient support and a camera configured to acquire image data of a patient positioned on the patient support. The system also includes a monitoring device in communication with the camera, wherein the monitoring device comprises a memory storing instructions that, when executed by a processor of the monitoring device, cause the monitoring device to receive the acquired image data; identify landmarks of the patient in the image data; track movement of the identified landmarks in the image data; and characterize a neuroactivity of the patient based on the tracked movement of the identified landmarks.

In another embodiment, a neuroactivity monitoring system is provided that includes a monitoring camera configured to acquire visible image data of a patient positioned on a patient support. The system also includes an infrared camera configured to acquire infrared image data of the patient positioned on the patient support. The system also includes a monitoring device in communication with the monitoring camera and the infrared camera, wherein the monitoring device comprises a memory storing instructions that, when executed by a processor of the monitoring device, cause the monitoring device to receive the acquired visible image data and the acquired infrared image data; identify facial and posture landmarks of the patient in the acquired visible image data; determine a physiological parameter based on the acquired infrared image data; and characterize a neuroactivity of the patient based on movement of the identified facial and posture landmarks and the physiological parameter.

In another embodiment, a method is provided that includes the steps of receiving image data of a patient; identifying one or more patient landmarks in the image data; tracking movement of the one or more patient landmarks over time in the image data; and determining that the movement of the one or more patient landmarks is indicative of a neuroactivity event

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
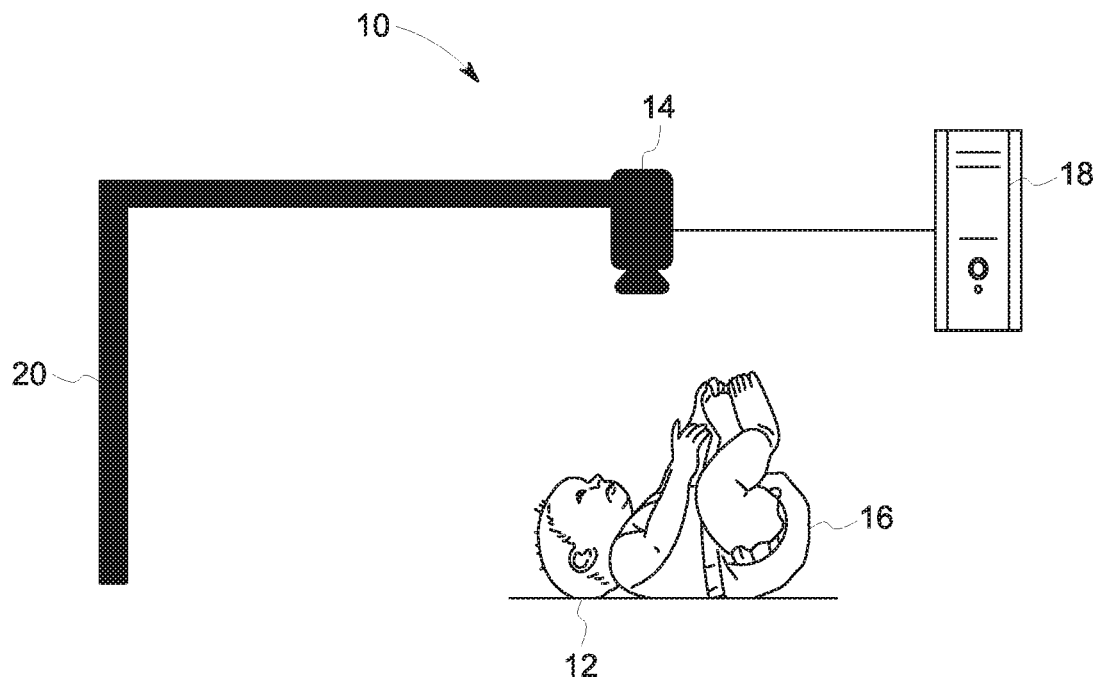
FIG. 1 is a view of an embodiment of a neuroactivity monitoring system, in accordance with an embodiment.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

Neonatal seizures are the common neurological emergency in the neonate and a serious concern for clinicians and parents worldwide. Many neonatal seizures are undetected in the busy Neonatal Intensive Care Unit (NICU) environment. Because seizures in infant patients may present differently than in adults, caregivers may miss fleeting or subtle signs of seizures. One method available to detect neonatal seizures is continuous multi-channel EEG monitoring. Interpretation of neonatal EEG involves a neurophysiologist or pediatric neurologist with specific expertise, who may not be available on a 24/7 basis. Also, positioning the multiple EEG electrodes on neonates is time-consuming, inconvenient, may be uncomfortable for the patient in a continuous monitoring scenario, and adds care-giving burden in the NICU.

The present techniques permit more accurate seizure detection via an infant image (e.g., video) monitoring and analysis system and method that may be used in conjunction with or instead of existing neonatal monitoring techniques. Provided herein are techniques that use acquired image data of the patient to generate information using facial and or body landmarks in the acquired image data, image facial recognition, eye deviation, respiratory rate detection, blood oxygenation detection, heart rate detection, sound detection, temperature variation detection from different skin areas, posture detection of limbs, and/or the pattern analysis of the body movement. The information generated from the image data may in turn be used to identify a seizure or other anomalous neuroactivity event. In an embodiment, the information generated from the image data may be used to assess brain growth and development and determine if infant development is progressing as expected or deviating from expected development. For example, the pattern analysis of body movement may be indicative of certain characteristic development stages or milestones.

In an embodiment, the disclosed techniques may be used in conjunction with continuous video EEG monitoring to identify physical manifestations of seizure in infants. The present techniques permit more rapid and efficient analysis of video data relative to manual review of the video data by an experienced caregiver as in conventional video EEG monitoring. In addition, the present techniques may be used as a less labor intensive precursor to determine if EEG and/or video EEG monitoring is recommended for a particular patient. That is, the present techniques may categorize a particular patient as being a candidate for additional monitoring via EEG or video EEG based on an initial video analysis of neuroactivity according to the present techniques. Hence, the proposed technology may be used to more efficiently distribute labor-intensive monitoring resources in a NICU setting.

As provided herein, the present techniques may be used in conjunction with available physiological monitoring information for the patient. In an embodiment, video analysis may be used for pain assessment in neonates. Pain assessment in neonates involves the observation of behavioral and physiological indicators as proxies for pain and is challenging in an infant population given that the current gold standard measure of pain—self-report—is un-achievable. Scales are constructed using multiple indicators and can be categorized as uni-dimensional, in which scales assess one indicator of pain, or multidimensional, in which scales assess multiple indicators of pain. Certain pain assessment scales assess both behavioral and physiological indicators of pain. The disclosed techniques may be used to isolate behavioral indicators of pain from acquired image data, resulting in more objective observation of behavioral indicators and, in turn, reducing the assessment error caused by individual provider variability. The system may also learn about the detectable manifestations of seizure or pain for that particular infant based upon the EEG signals. Once that system has learned these signals, the characteristic signals may be leveraged to detect subtle indications of seizure or pain that may not be otherwise detectable using other techniques.

Turning to the figures, FIG. 1 depicts an environmental view of an example of a neonatal assessment system 10 that includes a patient support 12, such as incubator or patient warmer. The system 10 also includes a camera assembly 14 that includes at least one camera (e.g., a visible light camera, an infrared camera, a combination camera, a 3D camera) that is oriented to acquire image data of the patient 16 via intermittent or continuous video monitoring. The camera assembly 14 may be in wireless or wired communication with a monitoring device 18 that receives the acquired image data. In one embodiment, the camera assembly 14 may be implemented to include a camera positioned above the patient 16 and a camera positioned on a side of the patient 16 to facilitate image acquisition of facial landmarks independent of a head angle of the patient 16. In another embodiment, the camera assembly may include a 3D camera. In another embodiment, the camera assembly 14 may include both visible light monitoring cameras and infrared cameras. Because the NICU may be a low light environment, the monitoring device 18 may be capable of arbitrating between infrared and visible light image data such that a best image data set is used as input to the analysis. The camera assembly 14 may permit sufficiently high resolution image acquisition to identify landmarks, e.g., facial landmarks, body landmarks, as provided herein.

The system 10 may include additional a base 20 for the camera assembly 14 that may be directly coupled to the patient support 12 or that is removable from the patient support 12 to permit the camera assembly 14 and monitoring device 18 to be used independently of a particular patient support unit. The base 20 may permit movement or adjustment of a position or orientation of the patient support 12 and/or the camera assembly 14 relative to one another and to a desired position to include the patient 16 in the field of view of the camera assembly 14 during monitoring. In addition, the patient support 12 may include one or more fiducials (e.g., marks or indicators with an easily resolvable pattern or image) used as a spatial reference. Because the patient support 12 and the camera assembly 14 may remain fixed in position relative to one another during monitoring, the movements of patient landmarks relative to one another and/or any fiducials may be used as part of image analysis to track movement, as provided herein. However, it should be understood that, in certain embodiments, the camera assembly 14 may be capable of reorienting during monitoring to keep the patient 16 in the camera field of view. For example, the patient 16 may be moved on the patient support during interaction with the caregiver, and it may be beneficial to adjust the camera orientation such that the camera assembly 14 is capable of capturing relevant patient landmarks.

Figure 2:
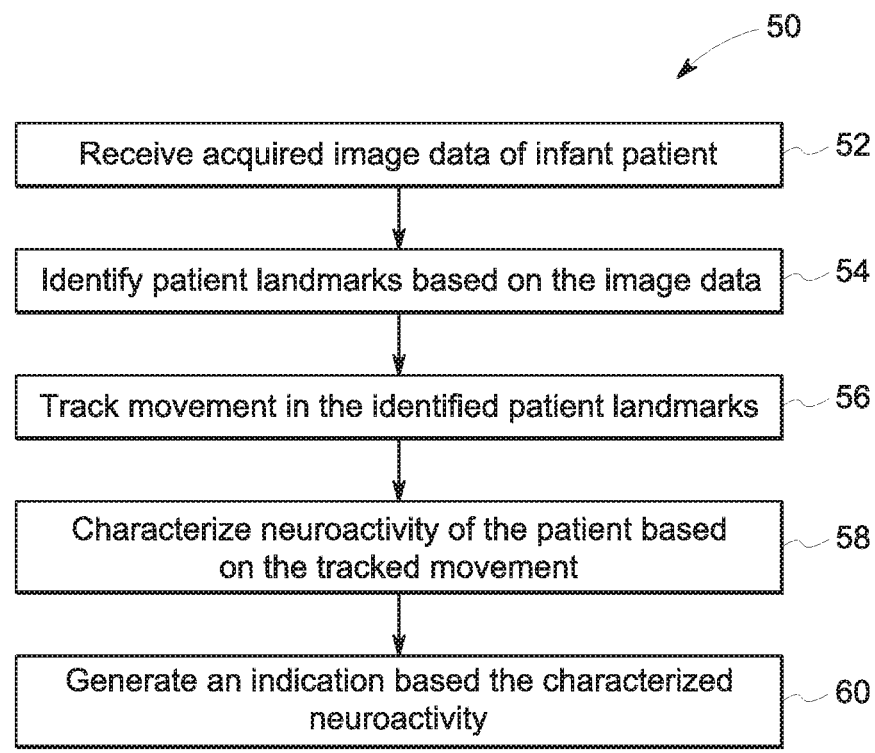
FIG. 2 is a flow diagram of a method of neuroactivity monitoring, in accordance with an embodiment.

FIG. 2 is a flow diagram of a neuroactivity monitoring method 50 according to the disclosed embodiments. Image data of the patient 16 is acquired (block 52) and assessed to identify one or more landmarks of the patient (block 54) that are resolvable in the image data. The patient landmarks may be physical features or regions of the patient 16 (e.g., facial features, limbs, chest). Identifying these landmarks facilitates tracking movement of individual patient landmarks between frames of the image data. By tracking the movement of an individual patient landmark and/or a group of landmarks (block 56), a patient's neuroactivity may be characterized (block 58). For example, a neuroactivity event such as a seizure may be identified. In another example, the characterization of the neuroactivity may be an estimate of the patient's pain level or an identification of a change in pain. The system may generate an indication based on the characterized neuroactivity (block 58). For example, the indication may be a report, an alarm, a displayed message, or a sound indicator. In another example, the indication may trigger instructions to another device to initiate a particular type of monitoring. In an embodiment, characterization of the neuroactivity as a seizure or a potential seizure may trigger video EEG monitoring to be initiated or may unlock or pair a video EEG monitoring device to the patient 16.

Figure 3:
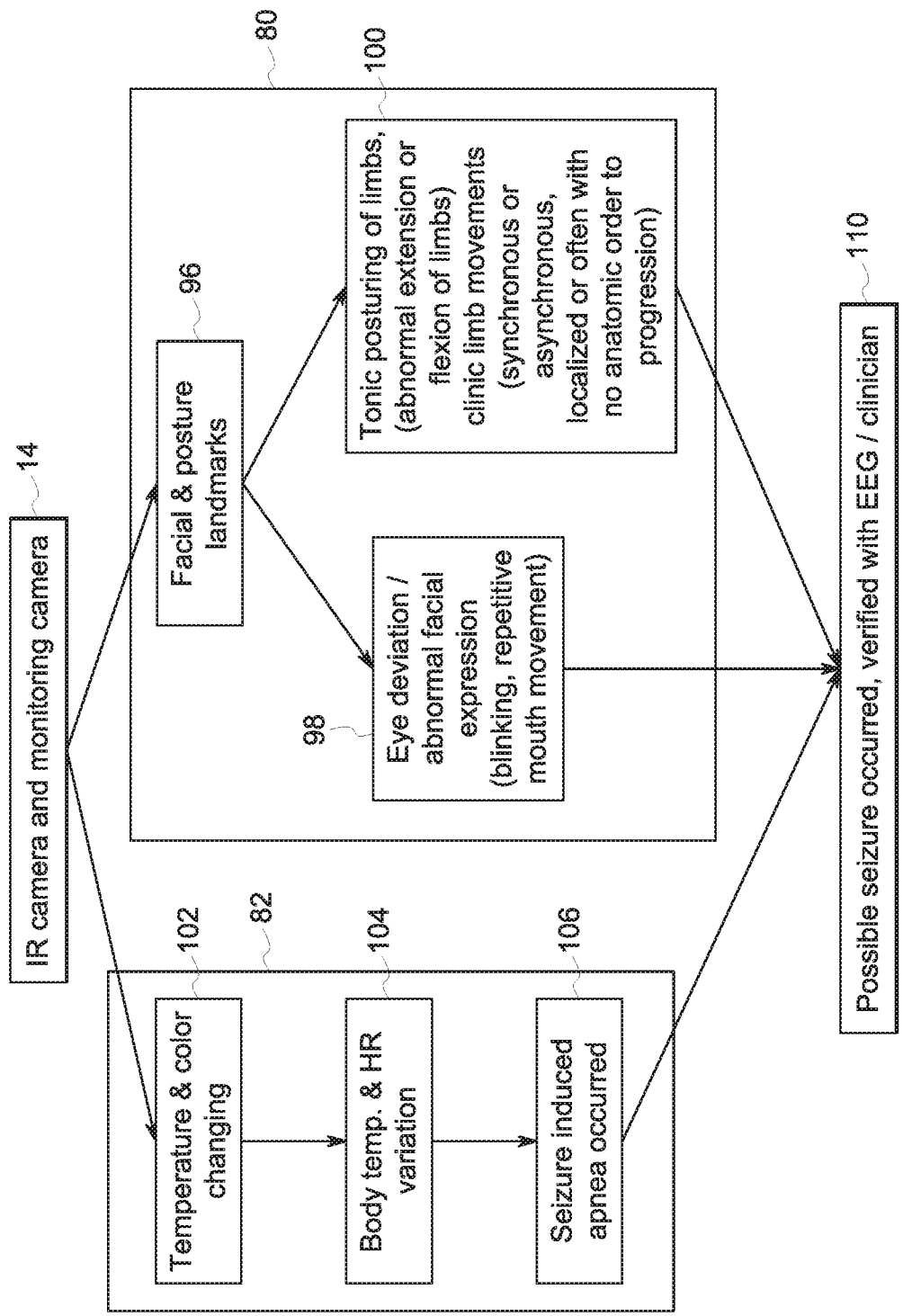
FIG. 3 is a schematic diagram of data inputs and outputs used in conjunction with neuroactivity monitoring, in accordance with an embodiment.

FIG. 3 is a schematic illustration of image analysis from image data acquired from the camera assembly 14. As discussed, the camera assembly 14 may include a visible light monitoring camera that acquires images of the patient over time. In an embodiment, the camera assembly may include an infrared camera that acquires infrared images of the patient over time. The images are used as input to a landmark detector and analyzer 80 executed by a processor of the monitoring device 18 (FIG. 1). In certain embodiments, the images are used as input to a physiological parameter calculator 82 executed by the processor of the monitoring device 18. The input images to the landmark detector and analyzer 80 and the physiological parameter calculator 82 may be one or both of the visible light images and the infrared images. In one embodiment, the landmark detector and analyzer 80 uses visible light images as a primary input while the physiological parameter calculator 82 uses infrared images as the primary input. In one embodiment, the landmark detector and analyzer 80 arbitrates between visible light and infrared images based on quality metrics. The landmark detector and analyzer 80 uses image data to perform detection and tracking that may include facial landmark assessments 98 and/or pose or limb-positioning assessments 100.

By way of example, the facial landmark assessments 98 may include identification of a head or face region of the patient, and detection of eyes, eyebrows, nose, and mouth landmarks within the identified face region. Once identified, the tracking may be based on the type of landmark and may include assessment of a degree, speed, and repetition cycle of the movement of each individual landmark. The eye movements tracked may be gaze direction changes of each eye in a same direction or different direction (moving in different directions at the same time) as the other eye, a speed of movement of the gaze direction for one or both eyes, or a blink rate. In particular, infants spend a majority of time with both eyes closed. However, changes in gaze direction underneath the eyelids are resolvable in image data. In this manner, seizure may be detected during wake or sleep cycles of the infant. The facial landmark assessments 98 may include mouth identification and tracking of repetitive lip movements indicative of sucking or swallowing. In addition, facial landmarks may be assessed as a group to identify abnormal facial expressions or facial expressions associated with pain.

By further way of example, the pose or limb-positioning assessments 100 may include identification of the arms, legs, hands, and feet as well as a trunk region of the patient. The pose or limb-positioning assessments 100 may include tracking a degree, speed, and repetition cycle of movement of an individual limb. In one example, tracking may be used to identify muscle contractions that cause the limb to jerk, which is observed in the image data as a rapid back-and-forth movement of the individual limb. Subregions of a limb may also be assessed, such as digit movements or hand/foot movements.

In addition, the movement of an individual limb may be assessed relative to other limbs. The assessment may include determination of whether multiple limbs are moving synchronously or asynchronously or whether particular movements are localized to a single limb or a single patient side (left/right). Further, a pattern of limb placement or moving between patterns of limb placement may be assessed. While infants have limited mobility, certain poses or limb arrangements may be common and identified as being of little clinical concern or an indication of infant growth and development, while other limb arrangements may be associated with an undesired neuroactivity event. In addition, certain successive pose combinations may be unusual and/or a cause for clinical concern. These changes may be different for different infants depending in clinical condition and/or age. In certain embodiments, the analyzer 80 is configured to detect changes, independent of a particular pose or expression.

In certain embodiments, the system includes a physiological parameter calculator 82 that uses image data as inputs to calculating one or more physiological parameters, such as heart rate, heart rate variability, respiratory rate, or temperature. Temperature assessment of individual landmarks and color changing parameters of individual landmarks or patient regions 102 may be based on visible and/or infrared image analysis of the patient. Visible light images and infrared images may be used to determine patient temperature 104. For certain patients, heart rate 104 may be determined based on tracking pulse movements of a face or trunk region using one or both of infrared and visible images. Respiration changes associated with apnea 106 may be resolvable in infrared images. Based on the outputs of the analyzer 80 and the physiological parameter calculator 82, a determination of an undesirable neuroactivity event 110, such as a seizure, may be made. The determination may trigger additional EEG monitoring or clinician intervention. It should be understood that, as provided herein, the analyzer 80 may be used with or without the physiological parameter calculator 82 to identify or characterize patient neuroactivity. However, where available, the physiological parameter calculator 82 may serve to augment or increase a confidence of a characterization of a particular neuroactivity event. For example, if a particular tracked movement is indicative of a seizure, the movement may be associated with a higher likelihood or higher confidence when coincident with a temporary elevated heart rate or respiration change.

Figure 4:
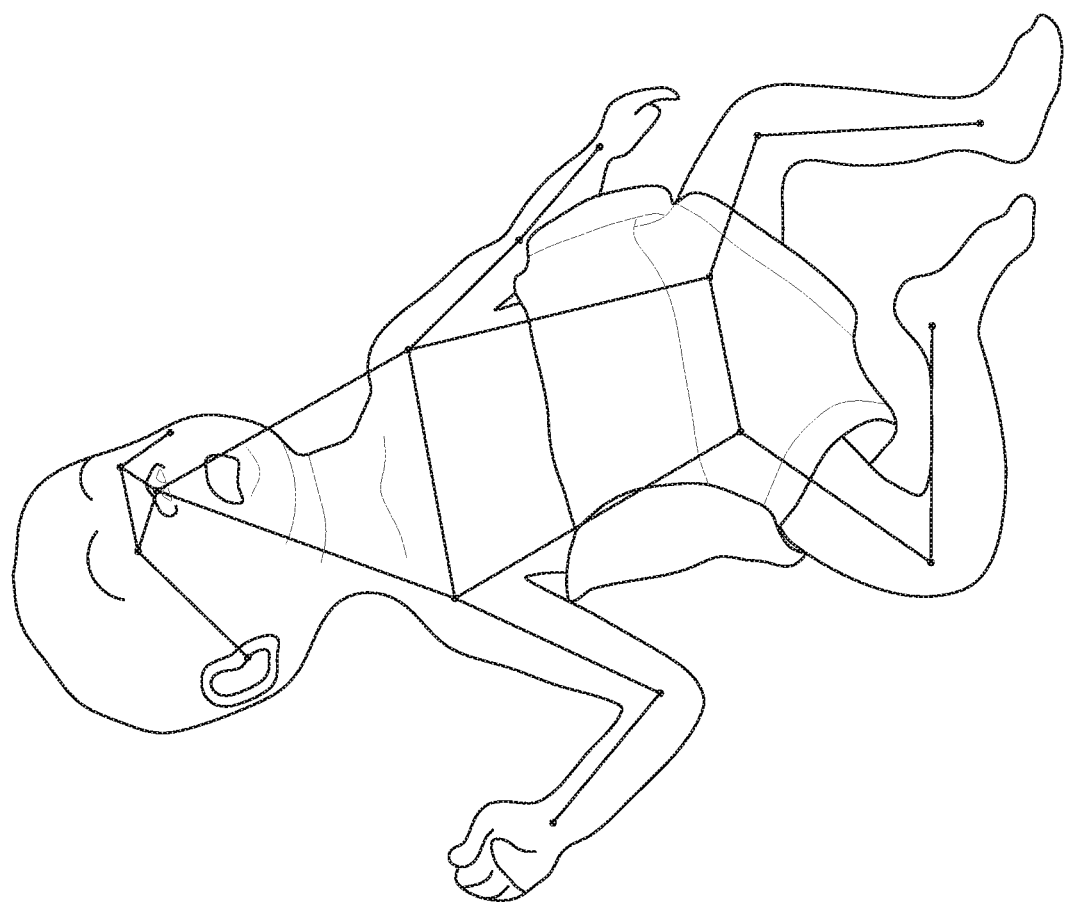
FIG. 4 is an example of identified facial and posture landmarks, in accordance with an embodiment.

It should be understood that the facial and/or body landmarks provided herein are by way of example, and the disclosed landmarks may be used alone or in various combinations. Further, the present techniques may be performed using more or fewer landmarks that in the disclosed embodiments. The identification of particular landmarks may be performed using suitable techniques. In one example, shown in FIG. 4, the body pose detection may be performed using a convolutional neural network to detect body landmarks that may include one or more of shoulders, elbows, wrists, hips, knees, ankles, nose, eyes, etc. Detection based tracking is used to analyze the pose change and find the movement patterns that match the body patterns of baby seizure. The detection model may be configured to account for and identify features that are commonly found on a patient support 12, such as a pad, wires or tubes extending away from the patient, etc.

Figure 5:
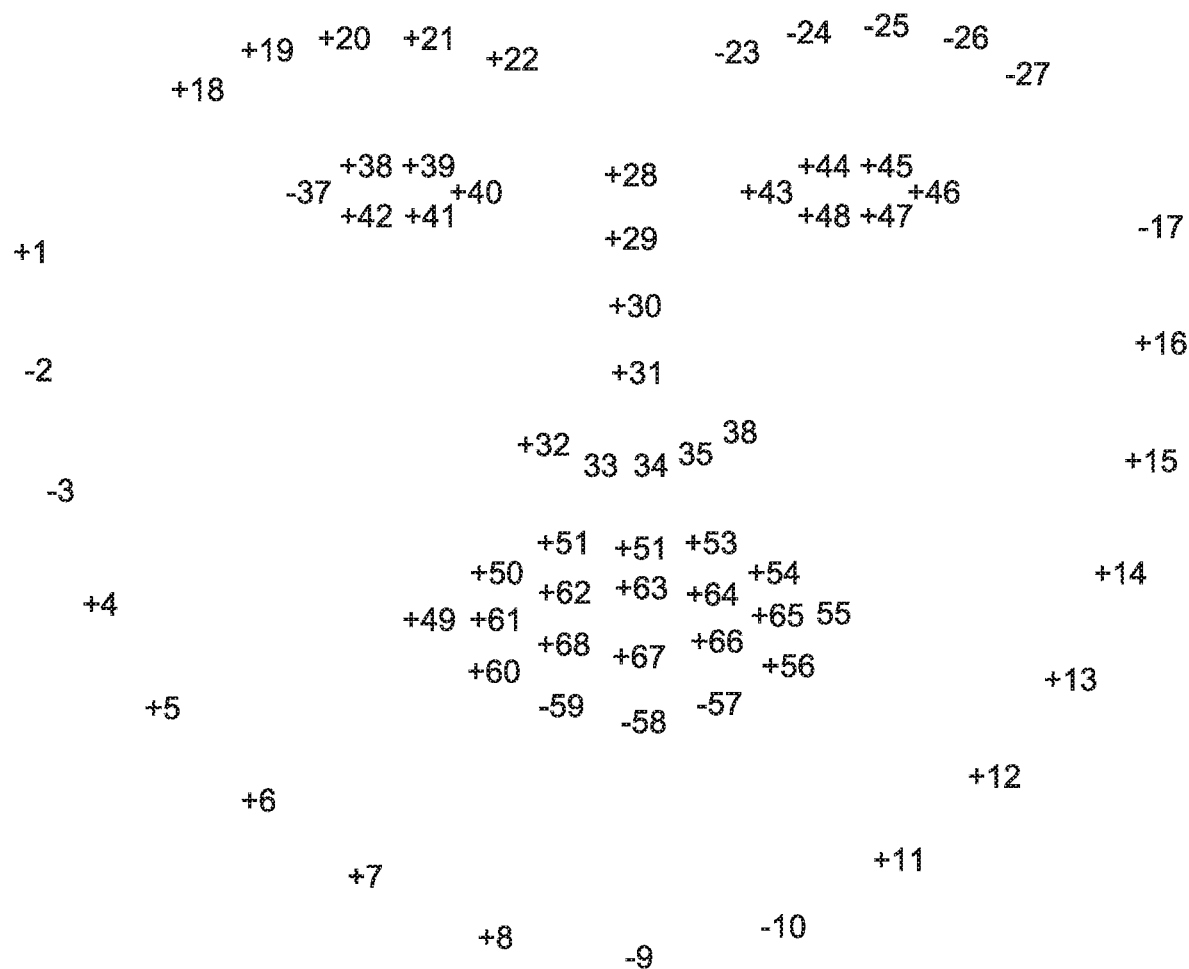
FIG. 5 is an example of identified facial landmarks, in accordance with an embodiment.
Figure 6:
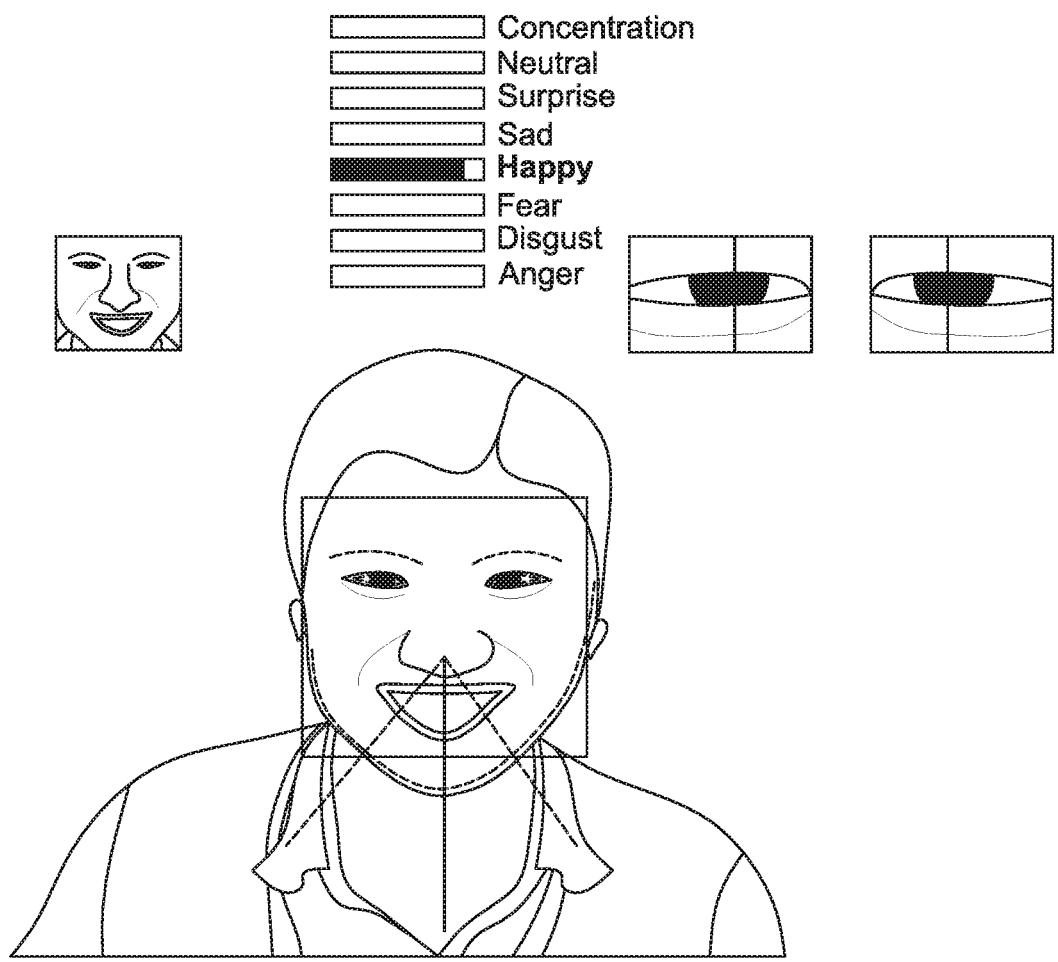
FIG. 6 is an example of facial expression analysis, in accordance with an embodiment.

FIG. 5 is an example of facial landmark detection that may be performed by the analyzer 80 in is a two-step process. In a first step, the face is localized in a given image. The face localization can be achieved using deep learning model or from the body pose detection result. A second step involves detecting the facial features inside the face region from step one. Given the face region, the facial feature detection uses convolutional neural network to detect key points for mouth, nose, jaw, eyes, eyebrows, etc. An eye blink detector uses the facial landmark model detected key points for eyes and eyebrows, and calculate the eye aspect ratio to determine eye blink. The eye tracking algorithm uses the detected eye landmarks and appearance-based gaze direction estimator to determine and track eye movement. The facial landmarks may be used in combination to characterize a patient expression, as shown in FIG. 6, as happy, neutral, or associated with surprise, which may be indicative of an undesired neuroactivity event. In certain embodiments, stability of facial expression may be associated with a lower likelihood of a seizure event. That is, regardless of the facial expression of the patient, rapid cycling between different facial expressions as identified by the analyzer 80 may be associated with an undesired neuroactivity event such as a seizure or a presence of pain. In one embodiment, an analyzer may use a preset threshold of expression changes to determine if the rate of expression cycling is associated with a seizure. The facial expressions can also be recorded and categorized as an indication of growth and development. For example, an expression of calm or happiness upon hearing the mother's voice may be indicative of a desired development milestone.

Figure 7:
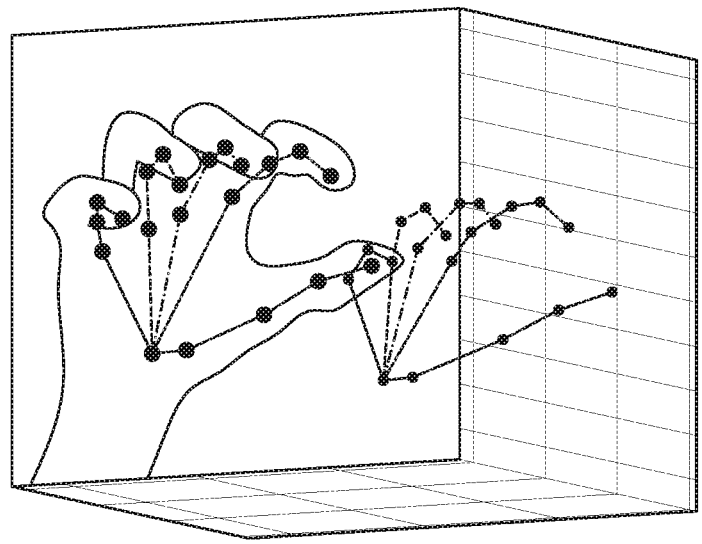
FIG. 7 is an example of a hand gesture analysis technique, in accordance with an embodiment.

FIG. 7 shows an example of hand gesture detection that may be used in conjunction with the disclosed embodiments. Similar to the facial landmark detection, a first step of hand gesture detection is detecting the hand bounding box using an independent deep learning model, or the bounding box may be derived from the body pose detection model. Then for the given hand region, the hand landmarks including fingertips, joints (distal interphalangeal joints, proximal interphalangeal joints, metacarpophalangeal joints), and wrists are detected by a convolutional neural network model. By tracking the hand landmarks movement, certain type of hand gestures that match the patterns of infant seizures are identified by the analyzer 80.

As provided herein, the outputs of the analyzer 80 and/or the physiological parameter calculator 82 and their confidence levels may be combined to generate an index that is used to identify or characterize patient neuroactivity. A scorecard metric may be used to measure the likelihood of the above-mentioned factors, and the conclusion that seizure detected is made if the overall score passes a certain preset threshold.

The determination and characterization may be based on characteristic patterns of particular types of neuroactivity events. In one example, a clonic seizure may be distinguished from a myoclonic seizure based on a present or absence of detected rhythmic contractions of muscles in the face or limbs. Clonic seizures may be identified based on repetitive, rhythmic (1-4/s) contractions of muscle groups of the limbs, face or trunk that are focal or multifocal while myoclonic seizures exhibit isolated or repetitive contractions of proximal or distal muscles, less regular and persistent than clonic jerks. generalized, focal or multifocal. Accordingly, the analyzer 80 may detect contractions of the limbs that present as jerking motions of the limbs. However, based on the location, number of sites, and repetition cycle, not only may a seizure be identified, but the type of seizure may be indicated. In another example, tonic seizures may be identified based on generalized or focal pose changes, sustained, but transient, asymmetrical posturing of the trunk or extremities, tonic eye deviation, or generalized bilateral symmetrical tonic posturing (with flexor/extensor predominance or mixed). Subtle seizures may be identified based on analyzer detection of motor automatisms (such as chewing, swallowing, sucking, repetitive tongue movements, "cycling", "boxing", "pedaling", "swimming") and autonomic signs (changes in heart rate, heart rate variability, or breathing pattern, flushing, salivation, pupil dilatation).

Recognizing neonatal pain is a challenge to nurses working with newborns due to the complexity of the pain phenomenon. Pain is subjective, and infants lack the ability to communicate, thereby making their pain difficult to recognize. Lack of consistency in pain assessment and personal attitudes about pain have been identified as concerns in the Newborn Intensive Care Unit (NICU). There are pain scales used to assess pain; however, there are variations in the methods and scales used, and there is not a universal method to assess pain in this population. Objective measurements including heart rate, blood pressure, respiratory rate, and salivary cortisol can be used, but many care providers usually rely on grimace, crying, and overall demeanor which is a subjective measurement. Therefore, there are significant differences between provider's level of training and experience in the recognition of pain. The present techniques may use the outputs of the analyzer 80 and the calculator 82 to objectively characterize a patient pain level as part of a pain scale and to alert caregivers if pain intervention is recommended or if pain intervention can be reduced.

As provided herein, the present techniques may employ a patient-specific model that includes data related to known seizure or known pain events for the patient. For example, based on video EEG data, the patient's typical outward responses to a seizure may be identified. Those responses, such as pose pattern, expressions, repetitive motions, may feed into the patient-specific model as inputs. Similarly, for events during which the patient experiences discomfort, such as during a medical intervention, the pain responses may be recorded and provided to the model. In this manner, a patient-specific model may be built and updated over the course of monitoring. However, where a patient-specific model is unavailable, a universal or standard model may be accessed by the system based on the patient's age, size, and/or clinical condition.

Figure 8:
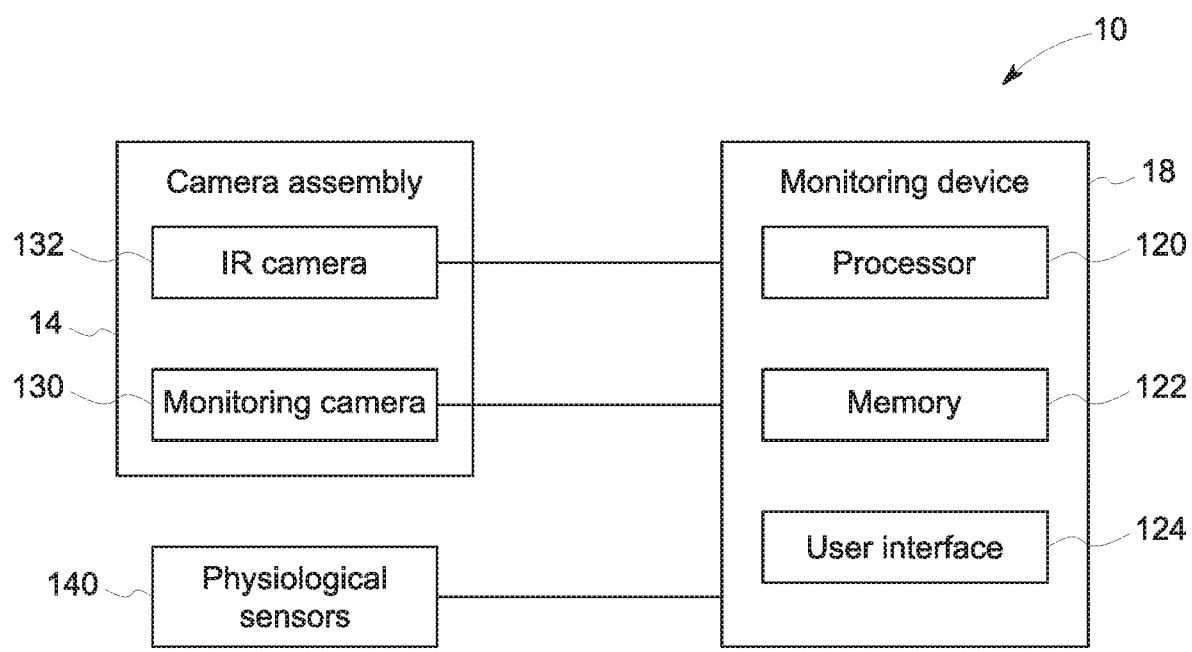
FIG. 8 is a block diagram of a neuroactivity monitoring system, in accordance with an embodiment.

FIG. 8 is a block diagram of the neuroactivity monitoring system 10 that includes the coupled to the incubator 10. Specifically, the system 10, includes a monitoring device 18 that includes a processor 120, and a memory 122 (e.g., a tangible, non-transitory, and computer-readable medium/memory circuitry) communicatively coupled to the processor 120, storing one or more sets of instructions (e.g., processor-executable instructions) implemented to perform operations related to the system 10. The monitoring device 18 also includes an operator interface 124 (e.g., keyboard, soft keys, touch screen, display) that permits an operator to provide operator inputs and that provides a display or other indication interface related to outputs of the system 10. For example, the operator may be able to provide inputs to the system 10 that a seizure is occurring based on clinical experience and observation. The input may be provided to the system 10 and used to update the determination processes (e.g., determination of an undesirable neuroactivity event 110, FIG. 3). The memory 122 may include volatile memory, such as random access memory (RAM), and/or non-volatile memory, such as read-only memory (ROM), optical drives, hard disc drives, or solid-state drives. Additionally, the processor 120 may include one or more application specific integrated circuits (ASICs), one or more field programmable gate arrays (FPGAs), one or more general purpose processors, or any combination thereof. Furthermore, the term processor is not limited to just those integrated circuits referred to in the art as processors, but broadly refers to computers, processors, microcontrollers, microcomputers, programmable logic controllers, application specific integrated circuits, and other programmable circuits.

The monitoring device 18 controls (e.g., provide a drive signal, activate, deactivate, etc.) the camera or cameras of the camera assembly 14. In an embodiment the system includes a visible light monitoring camera 130 and, in certain embodiments, an infrared camera 132. Where available, the system 10 may receive data from one or more physiological sensors 140 coupled to the patient. The physiological sensors 140 may include a microphone. In an embodiment, a microphone may be integrated in the camera assembly 14 to provide acoustic data. These sensors 140 may additionally or alternatively provide physiological parameter input used in the characterization of neuroactivity.

Technical effects of the invention include improved identification and characterization of patient neuroactivity in infants. Neuroactivity events such as seizures may present differently in infants relative to adults and are challenging to monitor. The present techniques use noninvasively acquired image data to identify landmark features of the patient and track their movement over time. Tracking movement of a subset of landmarks associated with a particular neuroactivity event may permit less computationally intense image analysis relative to image comparison techniques. In certain embodiments, the image data may include an infrared image data set that provides physiological parameter information that may augment the identification and characterization.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A neuroactivity monitoring system, comprising:
a patient support;
a camera configured to acquire image data comprising video electroencephalography data of an infant positioned on the patient support; and
a monitoring device in communication with the camera, wherein the monitoring device comprises a memory storing instructions that, when executed by a processor of the monitoring device, cause the monitoring device to:
receive the acquired image data;
identify landmarks of the infant in the image data;
track movement of the identified landmarks in the image data; and
characterize a neuroactivity of the patient based on the tracked movement of the identified landmarks, wherein the landmarks comprise limbs of the infant arranged in a pose and hands detected in a defined hand bounding box comprising hand landmarks of finger tips, joints, and wrists, and wherein the neuroactivity is characterized as a seizure based at least in part on the tracked movement of the hand landmarks and limbs in a pattern.

2. The system of claim 1, wherein the landmarks further comprise facial features of the infant, and wherein the neuroactivity is characterized as the seizure based at least in part on a determination that an identified first eye and an identified second eye are moving in different directions simultaneously.

3. The system of claim 1, wherein the landmarks further comprise facial features of the infant comprising eyes, and wherein the neuroactivity is characterized as the seizure based at least in part on the tracked movement of a blink rate of the eyes.

4. The system of claim 1, wherein the monitoring device is configured to generate an indication to initiate video electroencephalography monitoring based on the characterized neuroactivity.

5. A neuroactivity monitoring system, comprising:
a monitoring camera configured to acquire visible image data comprising video electroencephalography data of an infant positioned on a patient support;
an infrared camera configured to acquire infrared image data of the infant positioned on the patient support; and
a monitoring device in communication with the monitoring camera and the infrared camera, wherein the monitoring device comprises a memory storing instructions that, when executed by a processor of the monitoring device, cause the monitoring device to:
receive the acquired visible image data and the acquired infrared image data;
identify patient landmarks of the infant in the acquired visible image data;
determine a physiological parameter based on the acquired infrared image data; and
characterize a neuroactivity of the patient based on movement of the identified landmarks and the physiological parameter, wherein the landmarks comprise limbs of the infant arranged in a pose and hands detected in a defined hand bounding box comprising hand landmarks of finger tips, joints, and wrists, and wherein the neuroactivity is characterized as a seizure based at least in part on tracked movement of the hand landmarks and limbs in a pattern.

6. The system of claim 5, wherein the neuroactivity is further characterized as a clonic seizure based on a pattern of rhythmic contraction of one or more of the identified landmarks that repeats every 1-4 seconds.

7. The system of claim 5, wherein the neuroactivity is further characterized as a myoclonic seizure based on a pattern of isolated contraction of one or more of the identified landmarks.

8. The system of claim 5, comprising one or more sensors in communication with the monitoring device, wherein the monitoring device receives data from the one or more sensors related to additional physiological parameters.

9. A method, comprising:
receiving image data of infant, wherein the image data comprises video electroencephalography data;
identifying one or more landmarks in the image data;
tracking movement of the one or more landmarks over time in the image data; and
determining that the movement of the one or more landmarks is indicative of a neuroactivity event, wherein the landmarks comprise limbs of the infant arranged in a pose and hands detected in a defined hand bounding box comprising hand landmarks of finger tips, joints, and wrists, and wherein the neuroactivity event is characterized as a seizure based at least in part on the tracked movement of the hand landmarks and limbs in a pattern.

* * * * *